United States Patent [19]
Chiba et al.

[11] Patent Number: 5,577,992
[45] Date of Patent: Nov. 26, 1996

[54] BENDABLE PORTION OF ENDOSCOPE

[75] Inventors: Toru Chiba; Kazuhiro Naganuma; Rensuke Adachi; Tetsuya Utsui, all of Tokyo, Japan

[73] Assignee: Asahi Kogaku Kogyo Kabushiki Kaisha, Tokyo, Japan

[21] Appl. No.: 317,547

[22] Filed: Oct. 4, 1994

[30] Foreign Application Priority Data

| Oct. 5, 1993 | [JP] | Japan | 5-249131 |
| Nov. 16, 1993 | [JP] | Japan | 5-286348 |
| Nov. 26, 1993 | [JP] | Japan | 5-296529 |
| Nov. 30, 1993 | [JP] | Japan | 5-299497 |
| Jul. 14, 1994 | [JP] | Japan | 6-161941 |
| Aug. 24, 1994 | [JP] | Japan | 6-199197 |

[51] Int. Cl.⁶ ..................................................... A61B 1/00
[52] U.S. Cl. ........................ 600/152; 600/139; 600/146; 600/116
[58] Field of Search .................................. 600/139, 140, 600/144, 146, 152, 114, 115, 116; 138/120, 118, 118.1

[56] References Cited

U.S. PATENT DOCUMENTS

| 3,799,151 | 3/1974 | Fukaumi et al. . | |
| 4,236,509 | 12/1980 | Takahashi et al. | 600/139 |
| 4,890,602 | 1/1990 | Hake | 600/144 |
| 4,930,494 | 6/1990 | Takehana et al. . | |
| 4,967,732 | 11/1990 | Inoue | 600/139 |
| 4,976,191 | 12/1990 | Suzumori et al. . | |
| 5,125,143 | 6/1992 | Takahashi . | |
| 5,140,975 | 8/1992 | Krauter | 600/152 X |
| 5,179,934 | 1/1993 | Nagayoshi et al. . | |
| 5,325,845 | 7/1994 | Adair | 600/114 |
| 5,452,395 | 9/1995 | Schichman et al. | 600/140 X |

FOREIGN PATENT DOCUMENTS

| 1255822 | 10/1989 | Japan | 600/152 |
| 1315675 | 12/1989 | Japan . | |
| 1304416 | 12/1989 | Japan . | |
| 3173371 | 7/1991 | Japan . | |
| 3286732 | 12/1991 | Japan | 600/152 |
| 5-15485 | 1/1993 | Japan . | |

*Primary Examiner*—Richard J. Apley
*Assistant Examiner*—Beverly M. Flanagan
*Attorney, Agent, or Firm*—Greenblum & Bernstein, P.L.C.

[57] ABSTRACT

A bendable portion for an endoscope includes a bending mechanism which minimizes the bendable portion diameter and allows a large degree of bending. A first bending mechanism embodiment uses fluid pressure in an axially oriented chamber in a elastic body of the bendable portion. Expansion restraining members are used to restrict the expansion of the bendable portion to only the axial direction, and to protect internal members in the bendable portion. A second bending mechanism embodiment uses a shape memory alloy coil encircling the elastic body of the bendable portion. The shape memory alloy coil is heated to define the shape of the bendable portion.

35 Claims, 17 Drawing Sheets

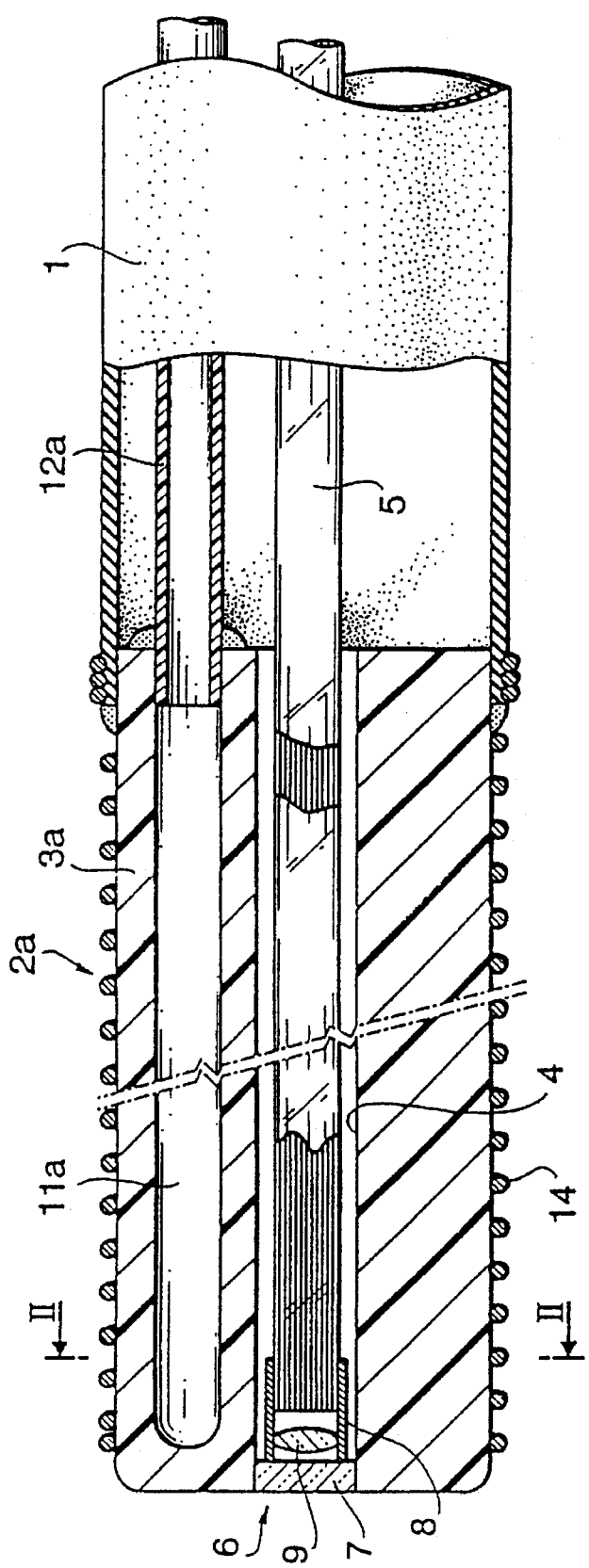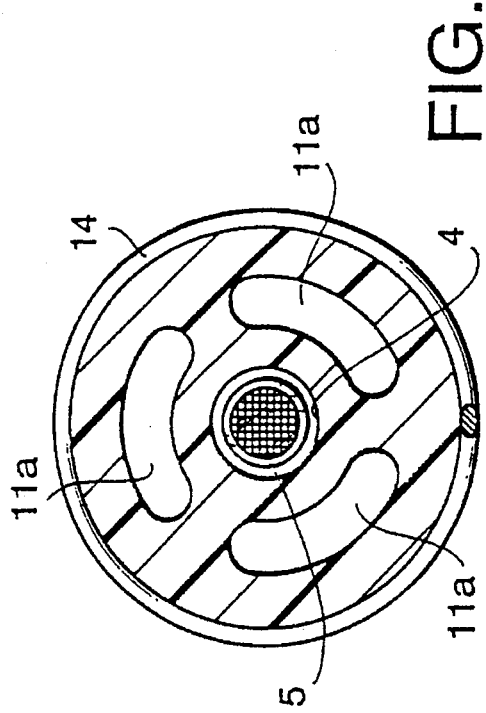
FIG. 1
FIG. 2

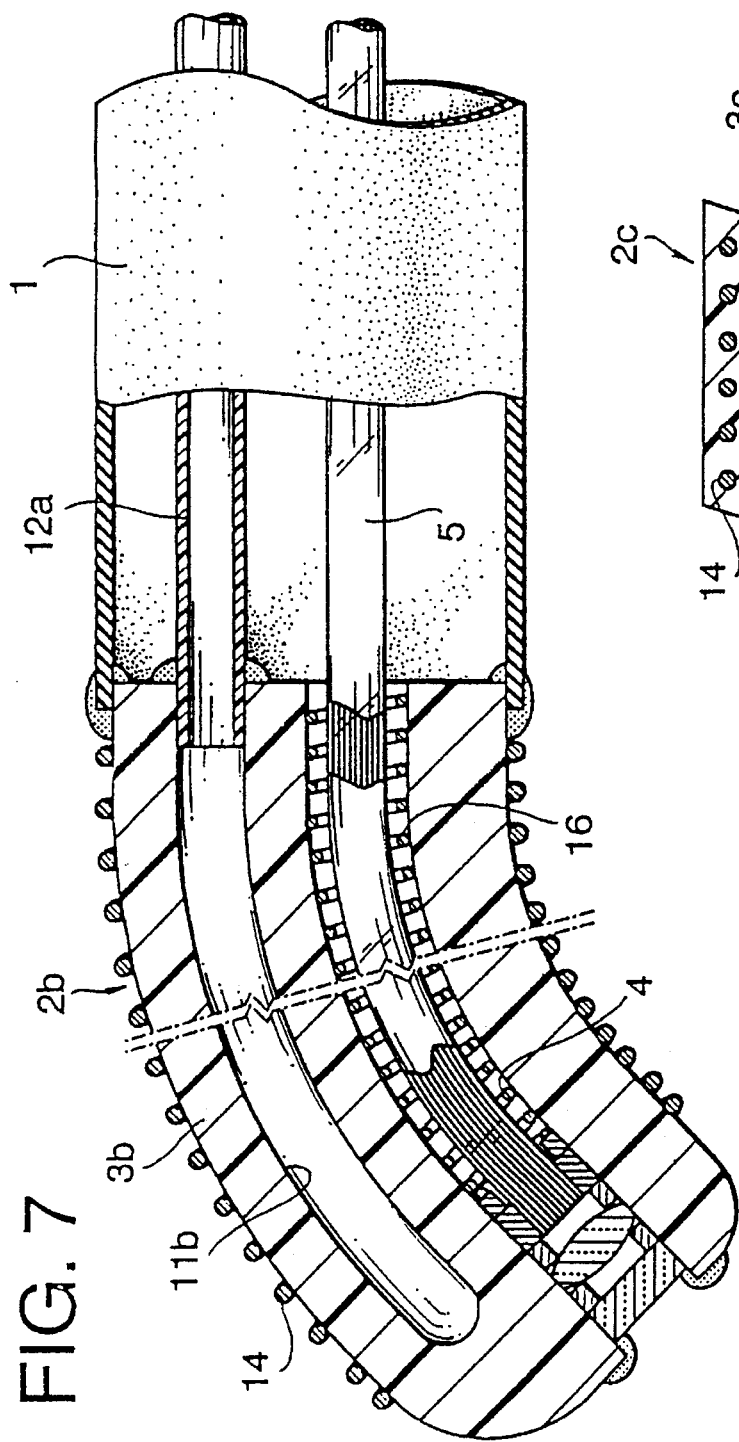
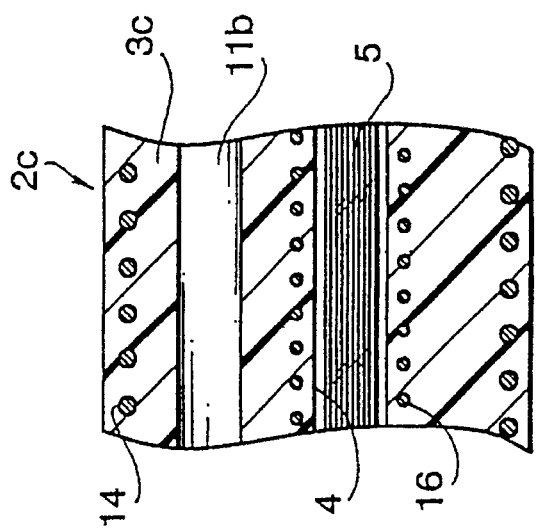
FIG. 7
FIG. 8

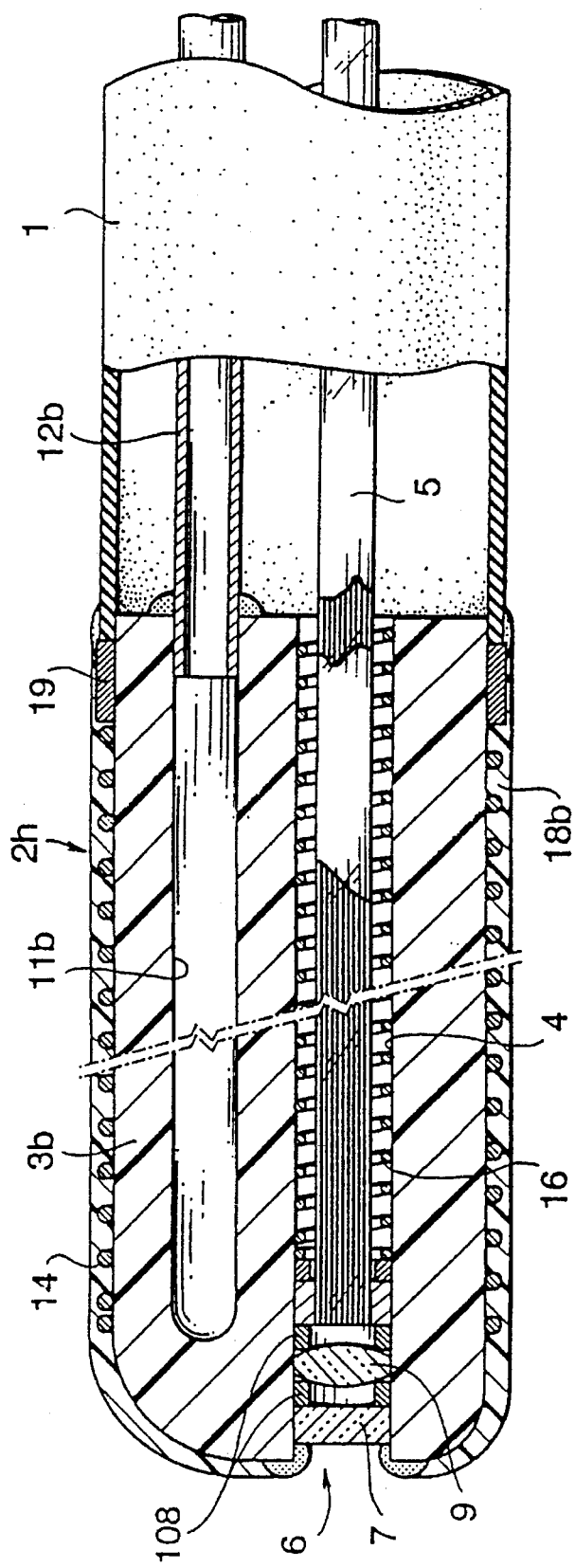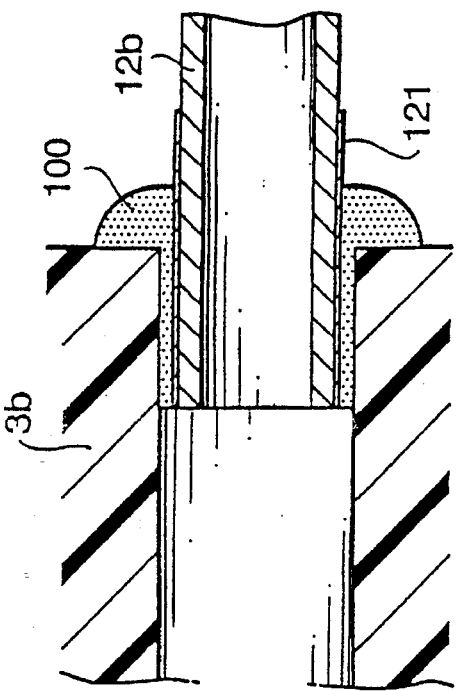

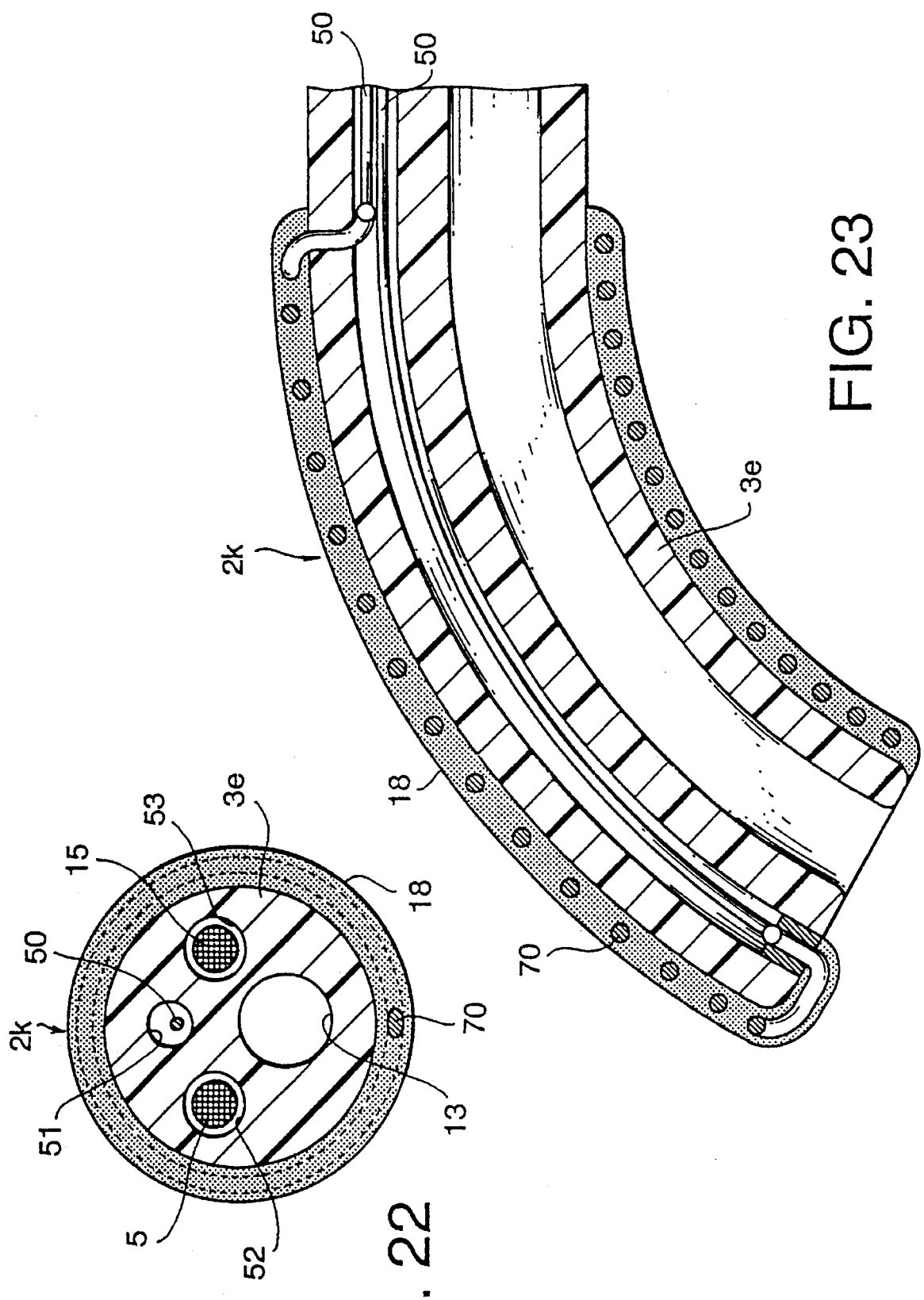

BENDABLE PORTION OF ENDOSCOPE

BACKGROUND OF THE INVENTION

The present invention relates to a bendable portion of an endoscope, using a bending mechanism to allow directional control of observation through the endoscope.

In general, a flexible endoscope useful for surgical procedures is provided with an insert tube, a bendable portion at the insertion end of the insert tube, and a control portion accessible to the operator.

Japanese Laid-open Patent Publication No. HEI 5-15485 discloses a bending mechanism for a bendable endoscope portion that uses a flat elastic sheet having a pressure chamber for bending the bendable portion. An operator controls a pumping mechanism to pump fluid into and out of the pressure chamber to expand and deflate the elastic sheet. Deformation of the elastic sheet in both vertical and lateral directions bends the bendable portion. However, since the diameter of the bendable portion changes when the elastic sheet deforms, it is difficult to make a slender bendable portion with this technique. Furthermore the bending mechanism disclosed in the above-mentioned publication cannot bend the bendable portion to a large angle relative to its own length.

SUMMARY OF THE INVENTION

It is therefore an object of the present invention to provide an improved benign mechanism for a bendable endoscope portion that allows the bendable portion to be a small diameter, and able to bend the bendable portion in a large angle relative to its own length.

Accordingly, to one aspect of the present invention, an improved bendable portion of an endoscope comprises an elastic body connected to an insertion tube and substantially formed as an elongated cylinder. A channel is provided through which an internal member is inserted and is formed through the elastic body in the axial direction of the elastic body. A pressure chamber formed in a peripheral portion of the elastic body is also provided, which is displaced from a central axis of the elastic body and parallel to the central axis. A fluid applying tube which is also provided is connected to the pressure chamber for pressurizing and depressurizing the pressure chamber so that the pressure chamber expands and contracts and the elastic body bend. An expansion restraining member is also provided encircles the elastic body, such that the expansion restraining member prevents expansion of the elastic body in a radial direction and allows expansion and contraction along the axial direction when the pressure chamber is pressurized and depressurized. Optionally, a plurality of pressure chambers are arranged around the central axis. Preferably, the expansion restraining member is a coil spring. The expansion restraining member may optionally be embedded in the elastic body.

According to another aspect of the present invention, the bendable portion further comprises a flexible outer skin, which covers the expansion restraining member.

According to still another aspect of the present invention, the bendable portion further comprises a crush-resistant member arranged around the internal member to protect the internal member during bending of the elastic body.

According to yet another aspect of the present invention, the bendable portion comprises an elastic body connected to an insertion tube and substantially formed as an elongated cylinder. A channel is provided through which an internal member is inserted and is formed through the elastic body along an axial direction of the elastic body. A pressure chamber formed in a peripheral portion of the elastic body is also provided, which is displaced from a central axis of the elastic body and parallel to the central axis, the pressure chamber is formed as a through channel completely blocked by a transparent member at a remote end of the bendable portion. A fluid applying tube is connected to the pressure chamber for pressurizing and depressurizing the pressure chamber so that the pressure chamber expands and contracts and the elastic body bends. The pressure chamber and the fluid applying tube are filled with a transparent liquid to transmit an illuminating light beam therethrough.

According to yet still aspect of the invention, a bendable portion of an endoscope comprises an elastic body, connected to an insertion tube and formed substantially as an elongated cylinder. A channel is provided through which an internal member is inserted, which is formed through the elastic body along an axial direction of the elastic body. A bending coil formed from a shape memory alloy wire is provided, which encircles the elastic body and the has a straight coil axis shape at a first predetermined temperature and a curved coil axis shape at a second predetermined temperature. A mechanism for heating the bending coil from the first predetermined temperature towards the second predetermined temperature so that the coil axis of the bending coil approaches the curved coil axis shape, the bending coil thereby bending the elastic body to a curved shape. Preferably, the heating mechanism applies electric current to the bending coil to heat the bending coil. Further preferably, the bending coil is completely covered by a flexible outer skin.

BRIEF DESCRIPTION OF THE DRAWINGS

FIG. 1 is a cross-sectional side view of a bendable endoscope portion according to a first embodiment of the present invention;

FIG. 2 is a cross-sectional front view taken along the line II—II in FIG. 1;

FIG. 7 is a cross-sectional side view of the third embodiment during bending;

FIG. 8 is a cross-sectional side view of a bendable endoscope portion according to a fourth embodiment of the present invention, illustrating a portion of the bendable portion;

FIG. 16 is a cross-sectional side view of a bendable endoscope portion according to a ninth embodiment of the present invention;

FIG. 17 is an enlarged view of a portion of FIG. 16;

FIG. 22 is a cross-sectional front view of the eleventh embodiment; and

FIG. 23 is a cross-sectional side view of the eleventh embodiment during bending.

DESCRIPTION OF THE EMBODIMENTS

Figure 3:
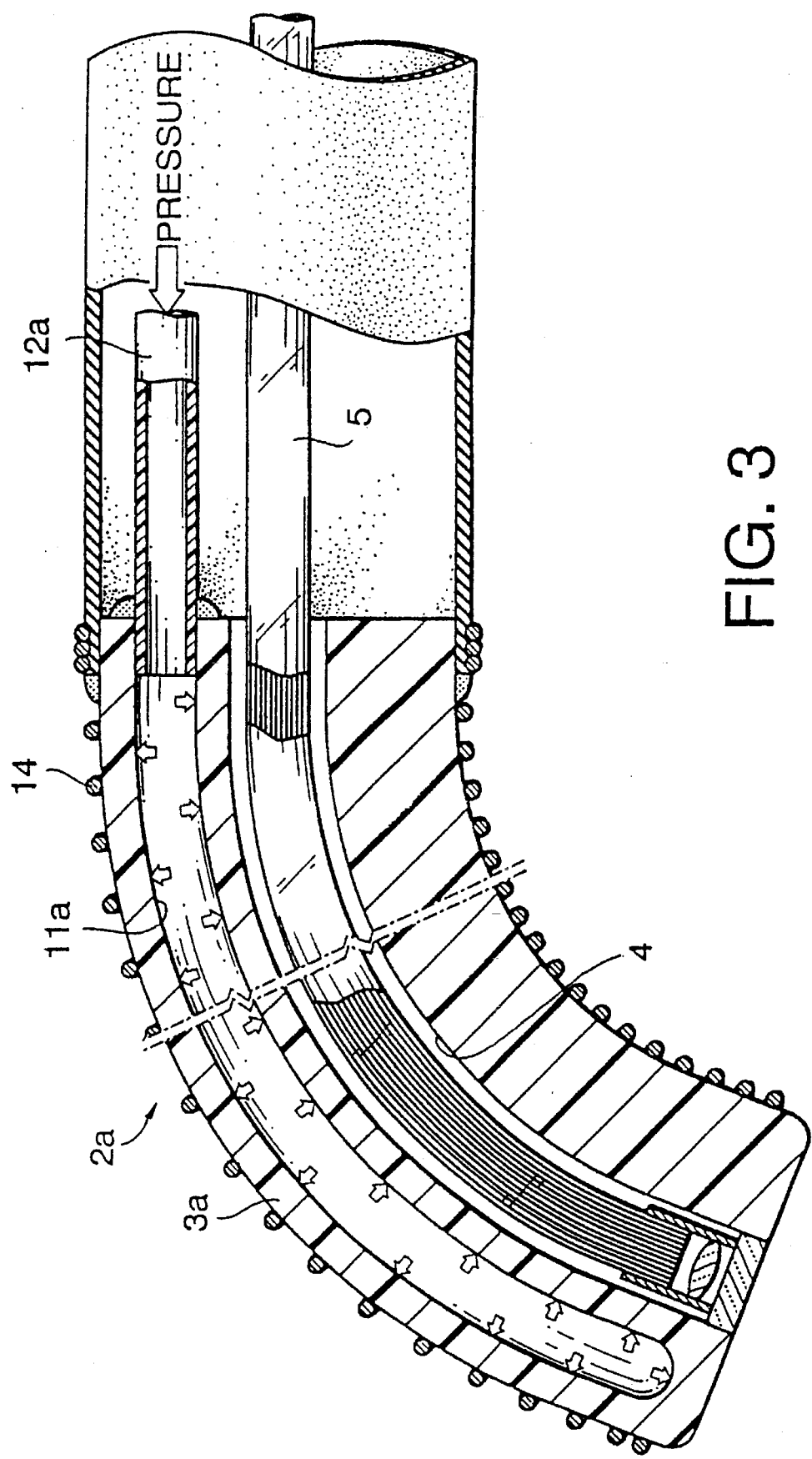
FIG. 3 is a cross-sectional side view of the first embodiment during bending.

FIGS. 1 through 4 show a bendable endoscope portion according to a first embodiment of the present invention. As shown in FIG. 1, the endoscope comprises a flexible insert tube 1 and a bendable portion 2a. The connection between the bendable portion 2a and the insertion end of the flexible insert tube 1 is watertight. The bendable portion 2a comprises which, and the elastic body 3a is flexible and bendable to any angle.

The elastic body 3a is formed from an elastomer material. Preferably, the elastic body 3a is formed from silicon rubber having an expansion ratio range from 300% to 400%. Alternatively, chloroprene rubber with a similar expansion ratio range may be used. The elastic body 3a is formed as an elongated cylindrical shape. The preferred embodiment of a bendable portion 2a of an endoscope has an elastic body 3a which is 4 mm in diameter and preferably 40 mm in length.

A through channel 4 is formed through the elastic body 3a for inserting an image guide fiber bundle 5. The fiber bundles described herein are conventional bundles of transparent optical fibers. An observing window 6 is defined by the end opening of the through channel 4, and is covered by a watertight cover glass 7 attached to the elastic body 3a. A lens frame 8 is attached inside the cover glass 7. Both the end of the image guide fiber bundle 5 and an objective lens 9 are fixed in the lens frame 8.

Although a light guide fiber bundle is not shown in FIG. 1, an illumination fiber bundle may be arranged in the through channel 4 or in another channel. Moreover, an image receiving element like a CCD may be used instead of the image guide fiber bundle 5. The elastic body 3a further comprises three elongated pressure chambers 11a, radially distributed as shown in FIG. 2. Each pressure chamber 11a is formed peripherally in the elastic body 3a, and are radially distributed about the axis of the elastic body 3a at 120-degree angle intervals. As shown in FIB. 2, each pressure chamber 11a is kidney-shaped in cross-section, and is curved along the outer circumference of the elastic body 3a.

As shown in FIG. 1, each elongated pressure chamber 11a is formed in the elastic body 3a with the entrance of the chamber 11a opening towards the attachment side of the elastic body 3a. A fluid applying tube 12a is hermetically fit to the inside wall of each pressure chamber 11a, at the chamber 11a entrance, and is sealed with a pressure-resistant seal.

The supply ends of the fluid applying tubes 12a are connected to a pumping device (not shown) for applying a fluid such as air. The pumping device is arranged at a control portion connected to the operator end of the insertion tube 1.

A radial expansion restraint 14 encircles the length of the elastic body 3a to counteract deformation of the elastic body 3a in a radial direction. The radial expansion restraint 14 is preferably a coil spring surrounding the elastic body. In the preferred embodiment of a bendable portion of an endoscope, the inner diameter of the coil spring fits the outer diameter of the elastic body 3a. The coil spring is preferably formed from a 0.3 mm diameter stainless steel wire.

The radial expansion restraint 14 can bend along its coiled length and can be stretched along its coiled length, the direction of its coiled length corresponding to the axial direction of the elastic body 3a. The radial expansion restraint 14 is constructed to maintain the same coiled diameter when the pressure chambers 11a are pressurized. Instead of the coil spring, a nylon fabric sheath may be used as a radial expansion restraint 14.

When a fluid in any one of the pressure chambers 11a is pressurized through its corresponding fluid applying tube 12a, the pressure chamber 11a expands, deforming the elastic body 3a. When one of the pressure chambers 11a is pressurized, the pressurized chamber 11a elongates in the axial direction ad the elastic body 3a bends away from the pressurized chamber side. When the added pressure in the pressure chamber 11 is removed, the pressure chamber is restored to its original form and the elastic body 3a straightens. Given the three-chambered construction, an operator can control the bendable portion 2a to bend in any direction by pressurizing any of the three evenly distributed pressure chambers 11a.

As described, the elastic body 3a may deform axially, but is restrained by the radial expansion restraint 14 from deforming in the radial direction. The deformation of the elastic body 3a is therefore restricted to the axial direction, and the bending of the elastic body 3a in response to the deformation of a pressure chamber 11a is increased. Thus, the elastic body 3a, and the entire bendable portion 2a, can bend to a large angle within a relatively small radius.

Figure 4A:
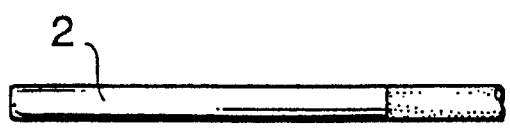
FIGS. 4(a) through 4(f) show bending conditions in various pressures of a bendable portion according to the first embodiment of the present invention.
Figure 4B:
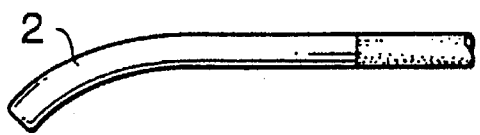
Figure 4C:
Figure 4D:
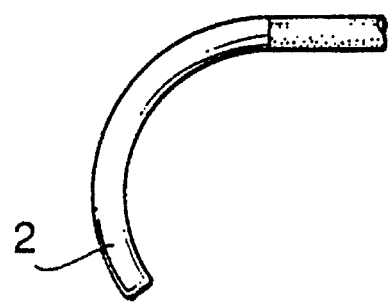
Figure 4E:
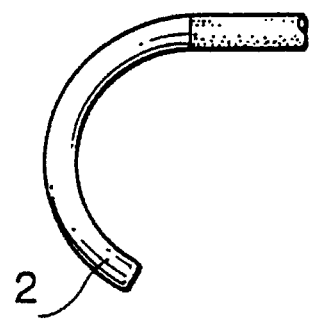
Figure 4F:
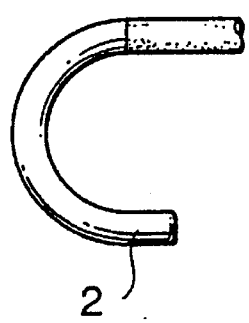

FIGS. 4(a) through 4(f) show the amount of bending of the bendable portion 2a in response to: 4(a) 1 atm (1 standard atmosphere), 4(b) 3.90 atm, 4(c) 4.5 atm, 4(d) 5.4 atm, 4(e) 6.8 atm, and 4(f) 9.0 atm. As shown in FIG. 4(d), when the pressure of any one of the pressure chambers 11a becomes 5.4 atmospheres, the bendable portion 2a bends by 90 degrees. At 9.0 atmospheres, shown in FIG. 4(f), the bendable portion 2a bends by more than 180 degrees.

The bendable portion 2a of an endoscope according to the first embodiment of the invention is therefore able to bend by a large amount in any direction, even though the bendable portion is slender. Furthermore, the use of the radial expansion restraint 14 allows a large degree of bending at reduced fluid pressures. If a radial expansion restraint such as the one described herein is not attached, the elastic body expands in the radial direction in addition to bending, and the bending angle per unit pressure is smaller than for the described embodiment.

The number of pressure chambers 11a is not limited to three according to the invention; i.e., there may be less than or more than three chambers. If there is only one pressure chamber 11a, the bendable portion 2a can bend in one direction by the amounts shown in FIGS. 4(a) through 4(f). If the bendable portion 2a has two chambers, the bendable portion 2a can bend in two directions by the amounts shown in FIGS. 4(a) through 4(f). If three or more chambers are provided, such as in the first embodiment, the bendable portion 2a can bend in any direction by the amounts shown in FIGS. 4(a) through 4(f).

Various embodiments of the invention, i.e., the second through eleventh embodiments, are hereinafter described. Portions appearing in the referenced drawings, but not described in the individual descriptions of the embodiments, are constructed similarly to those of the first embodiment.

Figure 5:
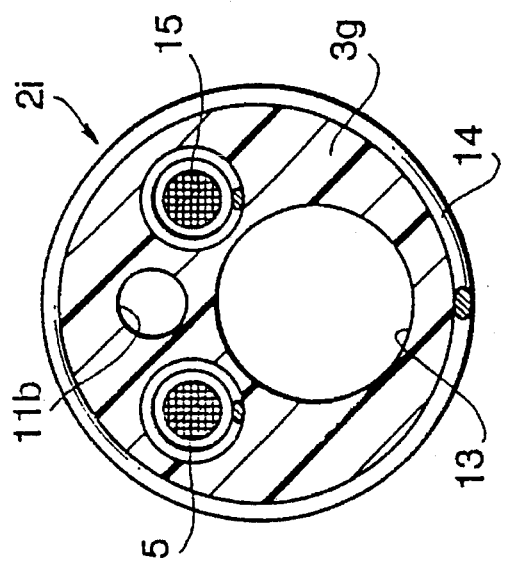
FIG. 5 is a cross-sectional front view of a bendable endoscope portion according to a second embodiment of the present invention.

FIG. 5 shows a second embodiment of a bendable portion 2i of an endoscope according to the present invention. The second embodiment has only a single pressure chamber 11b. However, the endoscope of the second embodiment is provided with an image guide fiber bundle 5 and a light guide fiber bundle 15 for illuminating an object. Additionally, the second embodiment comprises a forceps channel 13. A single pressure chamber 11b is provided in the elastic body 3g of the bendable portion 2i. The construction of the bendable portion 2i according to the second embodiment of the invention allows a very slender elastic body 3g to be used with the forceps channel 13. Preferably, the elastic body 3g is 2 mm in diameter.

Figure 6:
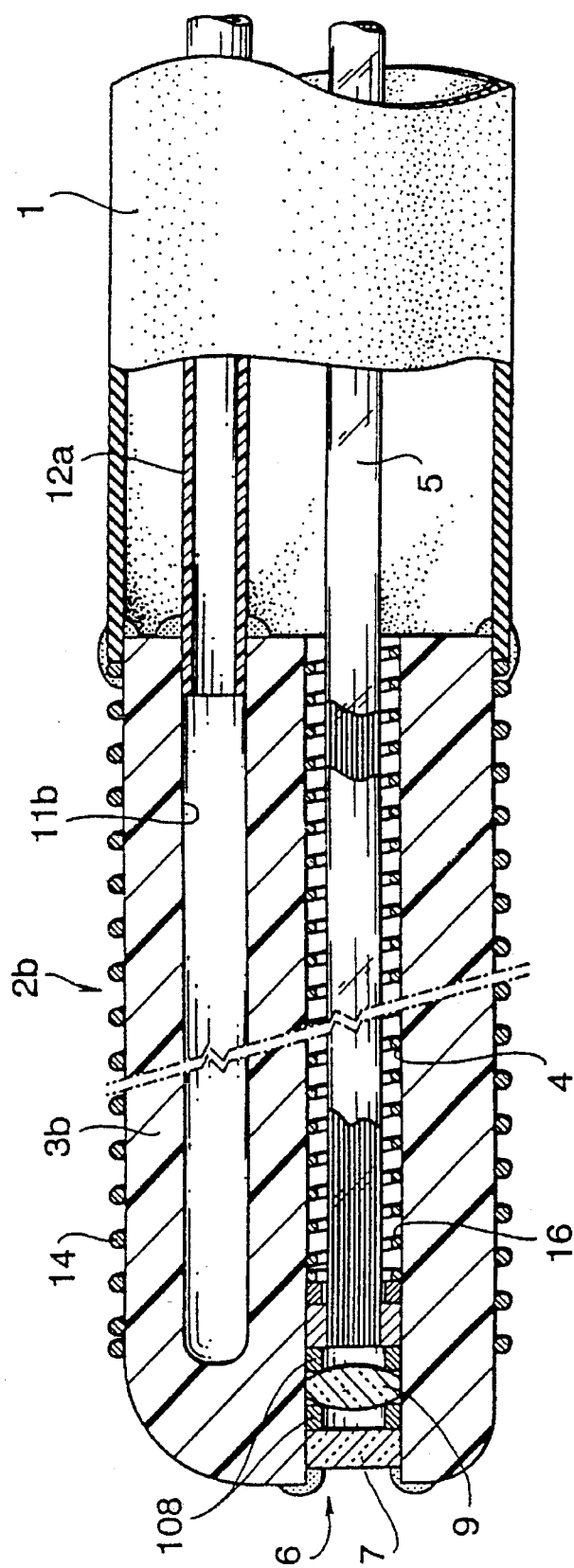
FIG. 6 is a cross-sectional side view of a bendable endoscope portion according to a third embodiment of the present invention.

FIG. 6 shows a third embodiment of a bendable portion 2b of an endoscope according to the present invention. The third embodiment is different in that a crush-resistant member 16 is provided in a through channel 4 to protect an internal member in the through channel 4.

Both the insert tube 1 and the fluid applying tube 12a of the third embodiment are flexible. An image guide fiber bundle 5 is inserted in the through channel 4 from the attachment end of the elastic body 3b. An observing window 6 is defined by the end opening of the through channel 4 and is covered by a watertight cover glass 7 attached to the elastic body 3. An objective lens 9 is positioned in the through channel 4 using spacers 108. The objective lens 9 is located between the image guide fiber bundle 5 and the cover glass 7. The cover glass 7 and the objective lens 9 are directly attached to the through channel 4 in the third embodiment. The elastic body 3b is encircled by the radial expansion restraint 14, as in the first embodiment. In this embodiment, the bendable portion 2b is preferably 2 mm in diameter and 20 mm in length. The inner diameter of the through channel 4 is preferably 0.35 mm.

A crush-resistant member 16 is arranged inside the through channel 4 to protect the image guide fiber bundle 5 from compression. The crush-resistant member 16 is preferably a coil spring shaped to fit the inner diameter of the through channel 4, and formed of a very small-gauge wire. In this embodiment, the coil spring has an outer diameter of 0.35 mm, and is formed from a 0.05 mm diameter stainless steel wire. When the fluid pressure in the pressure chamber 11b is increased by applying fluid through the fluid applying tube 12a, the chamber 11b is extended in the axial direction, and the bendable portion 2b bends as shown in FIG. 7.

The crush-resistant member 16 holds back the inner wall of the through channel 4, keeping the through channel 4 from compressing. Therefore, the image guide fiber bundle 5 is protected from any of the effects of the expansion of the pressure chamber 11b, as well as from the effects of bending when the bendable portion 2b bends. If the walls of the through channel 4 are allowed to exert a force on the image guide fiber bundle 5, the image guide fiber bundle 5 may be damaged after many bending cycles. The crush-resistant member 16 therefore prevents the image guide fiber bundle 5 from being damaged by the walls of the through channel 4. Furthermore, the crush-resistant member 16 may be used in any other channel, e.g., a forceps channel 13 or a light guide fiber bundle 15 channel as in the second embodiment, shown in FIG. 5.

FIG. 8 shows a bendable portion of an endoscope according to a fourth embodiment of the present invention. The fourth embodiment is a modification of the third embodiment, wherein the crush-resistant member 16 and the radial expansion restraint 14 are both embedded in the elastic body 3c. FIG. 8 shows only an intermediate portion of the elastic body 3c, illustrative of the differences of the fourth embodiment. In the fourth embodiment, both the radial expansion restraint 14 and the crush-resistant member 16 are embedded in the elastic body 3c. A bendable portion 2c of an endoscope according to the fourth embodiment of the invention therefore can be even more slender than the previously described embodiments. Furthermore, the eighth embodiment has a smooth outer surface, preventing damage to the surgical subject or to the endoscope. The radial expansion restraint 14 and the crush-resistant member 16 are not necessarily coil springs, but can be a set of parallel rings arranged at equally spaced intervals along the length of the elastic body 3c.

Figure 9:
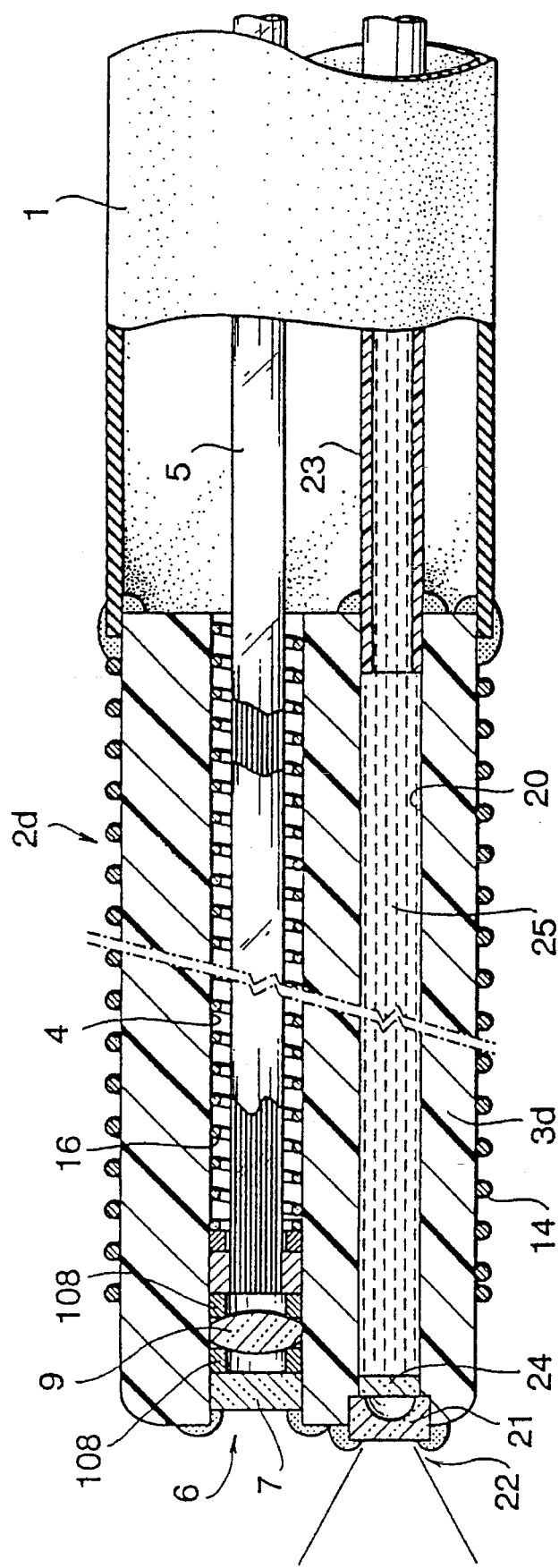
FIG. 9 is a cross-sectional side view of a bendable endoscope portion according to a fifth embodiment of the present invention.

FIG. 9 shows a bendable portion 2d of an endoscope according to a fifth embodiment of the present invention. The fifth embodiment of the present invention is different in that the pressure chamber 20 is bored completely through the elastic body 3d in the axial direction, defining an illuminating window 22 at the exit. The illuminating window 22 is blocked by a concave lens 21 and a watertight seal plate 24.

An endoscope of the fifth embodiment comprises a flexible insert tube 1. In the fifth embodiment, the bendable portion 2d is preferably 2 mm in diameter and 20 mm in length. A through channel 4 is formed in the elastic body 3d of the bendable portion 2d as in previous embodiments. The open end of the pressure chamber 20 is connected to a fluid applying tube 23.

An image guide fiber bundle 5, cover glass 7, objective lens 9, and spacers 108 are of the sane constitution as the third embodiment. A radial expansion restraint 14 and an crush-resistant member 16 are also arranged similarly to the third embodiment.

Figure 10:
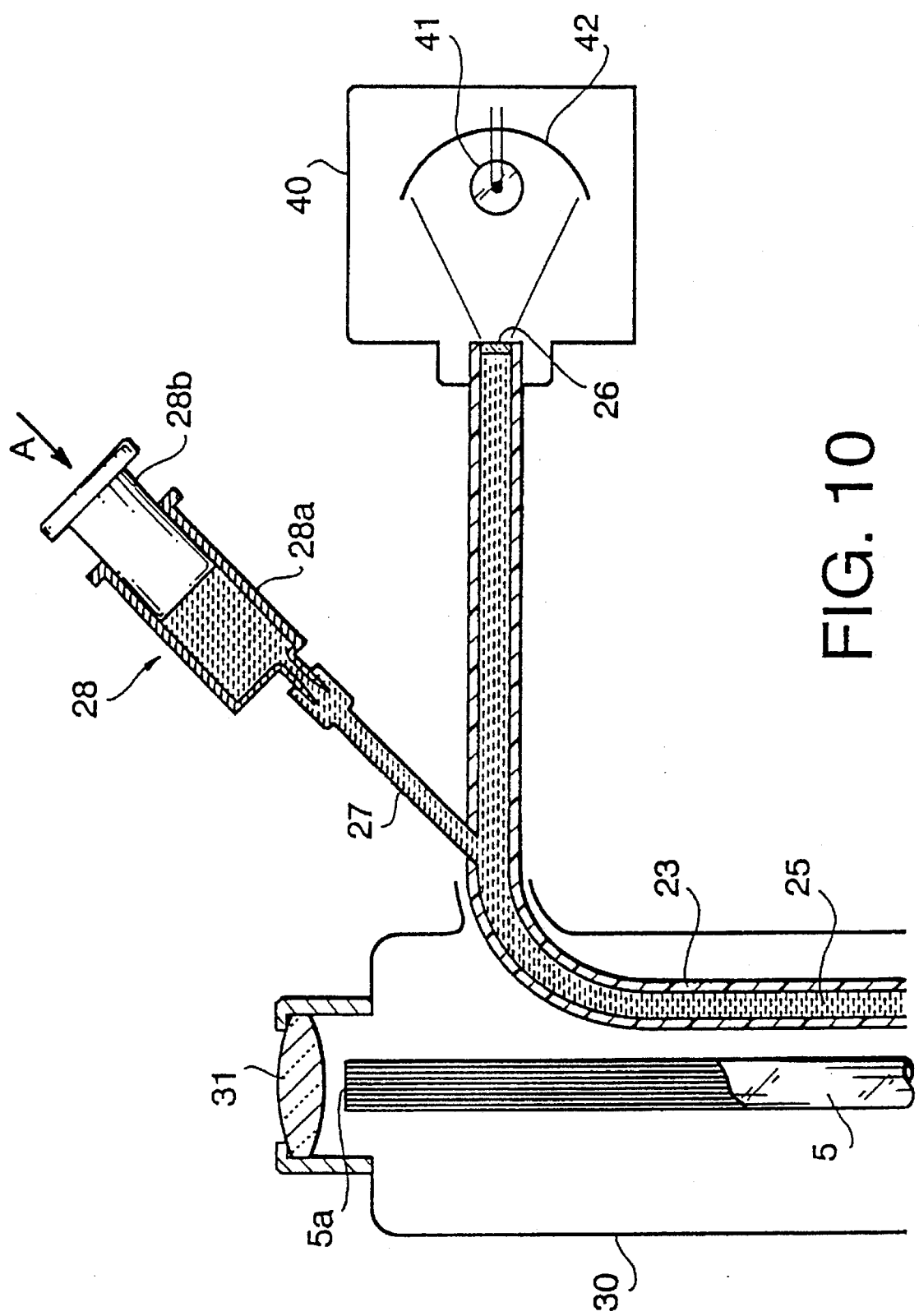
FIG. 10 is a schematic view of a control portion of a bendable endoscope portion according to the fifth embodiment of the present invention.

FIG. 10 shows a control portion 30 connected to the control end of the insert tube 1 of the fifth embodiment. An observing end 5a of the image guide fiber bundle 5 provides an exit for a guided image to proceed to an observing position of an eye piece lens 31.

The fluid applying tube 23 projects from the control portion 30, and is connected to a light source device 40. The pressure chamber 20 and the fluid applying tube 23 are completely (without air bubbles) filled by a transparent liquid 25. The light source device 40 is provided with a lamp 41 and a concave mirror 42 for converging the light emitted from the lamp 41. The light source end of the fluid applying tube 23 is sealed by a transparent plate 26 and is located at the convergent area of the light.

The light emitted from the lamp 41, converged by the concave mirror, impinges on the transparent plate 26, and is transmitted by the transparent liquid 25 in the fluid applying tube 23. The light then exits through the pressure chamber 20, the seal plate 24 and the concave lens 21 to illuminate an object or area for observation. That is, the fluid applying tube 23 and the transparent liquid 25 act as a light guide means for illumination.

Figure 11:
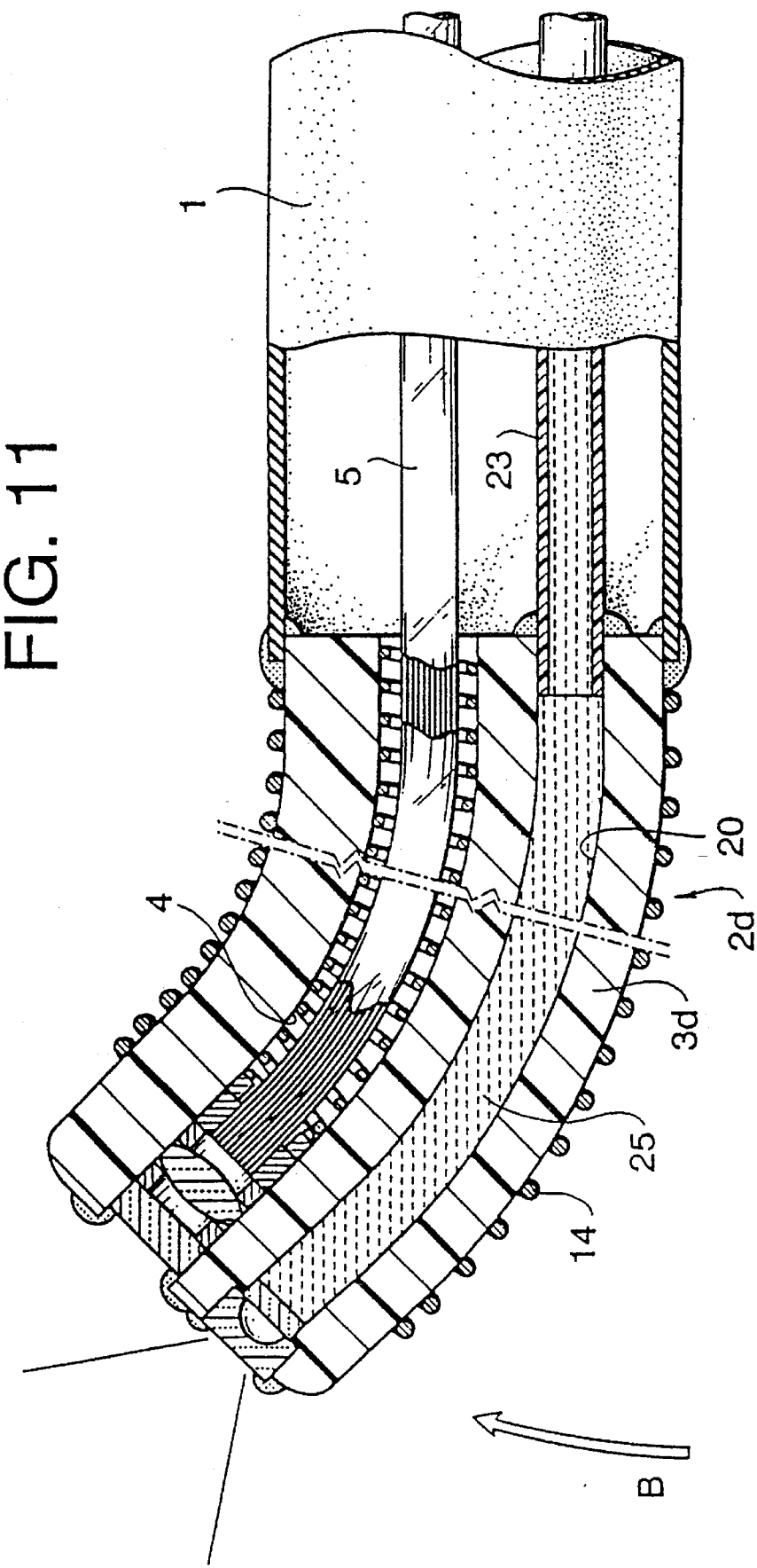
FIG. 11 is a cross-sectional side view of the fifth embodiment during bending.

A pressurizing tube 27, branching off from the fluid applying tube 23, is connected to a pressure device 28. The pressure device 28 is constructed similarly to a hypodermic syringe, and is provided with a cylinder 28a and a piston 28b. When the piston 28b of the pressure device 28 is pushed in the direction shown by an arrow A in FIG. 10, the liquid in the cylinder 28a is pushed out into the fluid applying tube 23. The pressurized liquid extends the pressure chamber 20 in the axial direction of the elastic body 3. The bendable portion 2d then bends as shown by an arrow B in FIG. 11. When the piston 28b is returned to the neutral position shown in FIG. 10, the extended pressure chamber 20 contracts and the bendable portion 2d becomes straight. The light from the lamp 41 is transmitted through the transparent liquid 25 and exits through the concave lens 21, illuminating the object or area, even as the bendable portion 2d bends in any direction.

Preferably, the fluid applying tube 23 should be formed from polyethylene, polyurethane or fluororesin, so that the expansion of the fluid applying tube 23 under pressure is small. The transparent liquid 25 is a biologically benign fluid. For instance, a silicon oil such as methyl silicon, phenylmethyl silicon or phenyl silicon is used.

If the fluid applying tube 23 is formed from a transparent material, it is preferable that the refractive index of the fluid applying tube 23 is lower than that of the transparent liquid 25, so that the transmitted light can be totally internally reflected by the boundary between the fluid applying tube 23 and the transparent liquid 25. Furthermore, the inner wall of the fluid applying tube 23 can be metal-coated to reflect light. If the inner wall of the fluid applying tube 23 is coated by a metal that acts as a mirror, the refractive index of the transparent liquid 25 does not need to be defined. The inner wall of the pressure chamber 20 may also be metal-coated with a mirror-like surface. The inner wall of the fluid applying tube 23 must be smooth, and the ratio of impurities in the transparent liquid 25 should be low, in order to reduce the transmission losses (of light) at the bendable portion 2d.

The light transmitted by the transparent liquid 25 diverges (spreads out) at the concave lens 21 and illuminates an object to be observed. The seal plate 24 is arranged in the pressure chamber 20 such that there is an air gap between the concave lens 21 and the seal plate 24. The difference of the refractive indexes at the air-lens boundary of the concave surface of the concave lens 21 is larger that if the transparent liquid 25 directly contacts the concave lens 2. The divergent angle of the light exiting from the concave lens 21 is therefore larger.

The fifth embodiment of a distal end of an endoscope according to the present invention therefore allows an extremely thin endoscope, as the illumination source and the bending actuator are combined. Furthermore, the illumination guide is a liquid, and is therefore not subject to bending stresses like a fiber optic bundle.

Figure 12:
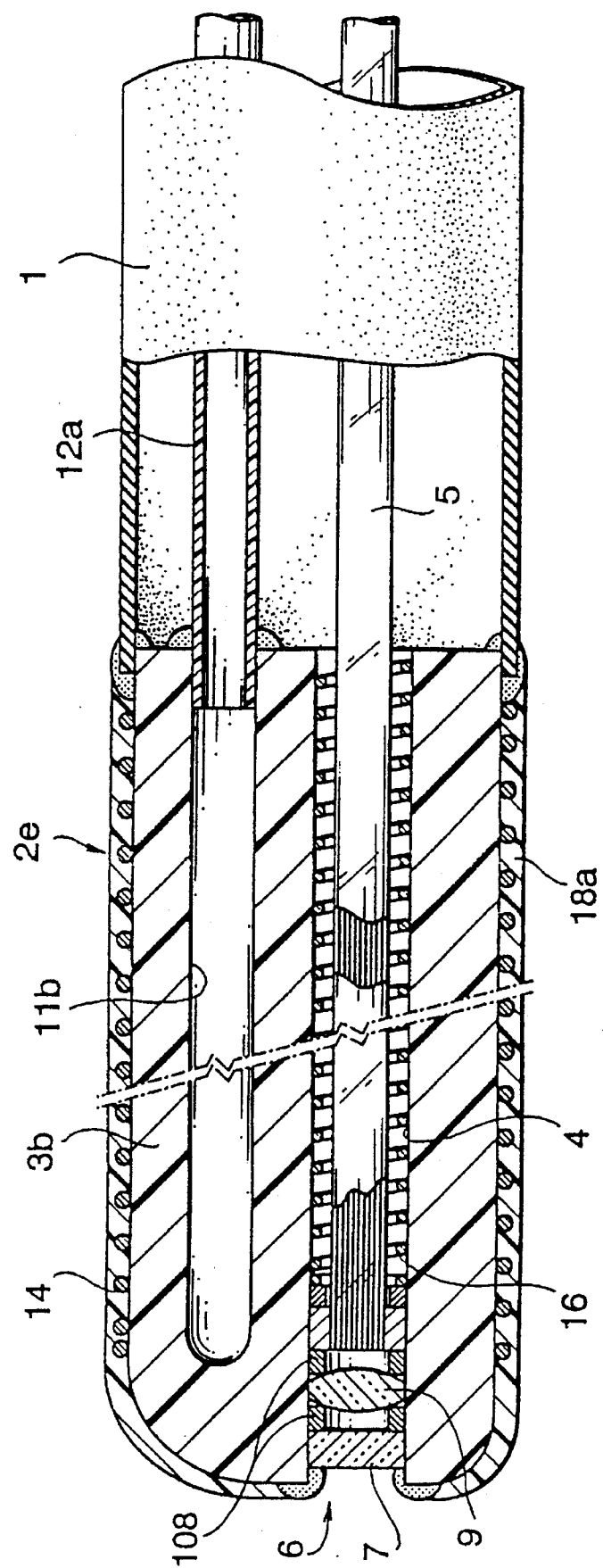
FIG. 12 is a cross-sectional side view of a bendable endoscope portion according to a sixth embodiment of the present invention.

FIG. 12 shows a distal end 2e of an endoscope according to a sixth embodiment of the present invention. The endo-scope of this embodiment is generally the same as the third embodiment shown in FIG. 6. The sixth embodiment is different in that the radial expansion restraint 14, encircling the elastic body 3b, is embedded in a flexible, water tight outer skin 14a. The flexible outer skin 18a is preferably formed from silicon rubber, chloroprene rubber, or a similar biologically benign elastomer. The flexible outer skin 18a is cemented to the bendable portion 2e, at least at the observing window 6 and at the attachment end of the bendable portion 2e, and has a hole for the observing window 6.

Further, the flexible outer skin 18a may be formed around the elastic body 3b by dipping, spraying, or brushing the bendable portion 2e with a polymerizing monomer. For example, the bendable portion 2e is dipped in silicon rubber such that the thickness of the flexible outer skin 18a exceeds the thickness of the radial expansion restraint 14 by about 0.1 mm. The outer skin 18a is thereafter cured in room temperature.

Figure 13:
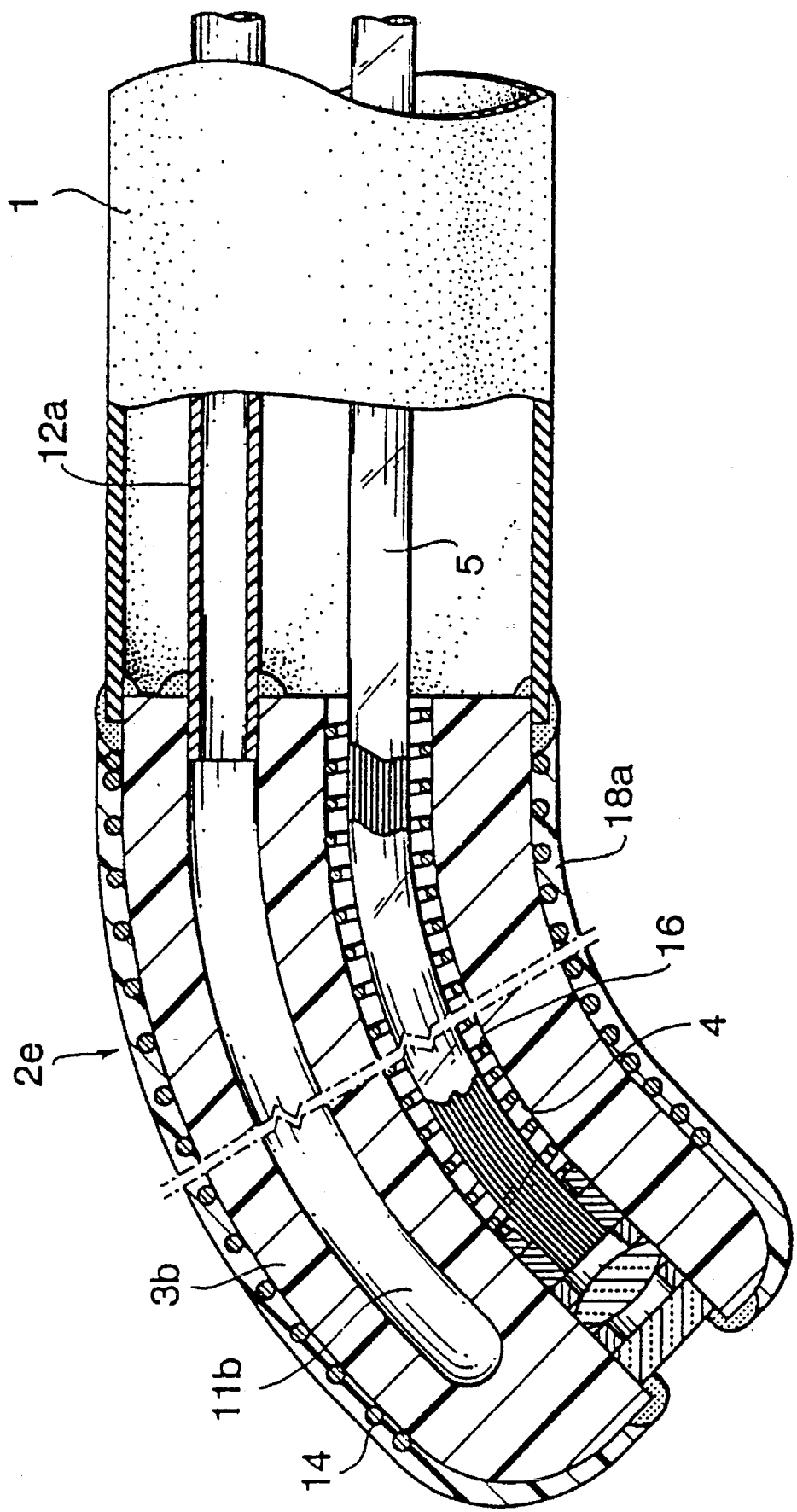
FIG. 13 is a cross-sectional side view of the sixth embodiment during bending.

When the fluid in the pressure chamber 20 is pressurized, the bendable portion 2e bends as shown in FIG. 13. In this fashion, the flexible outer skin 18a does not interfere with the bending of the bendable portion 2e. When the added pressure is removed, the extended pressure chamber 20 contracts, and the bendable portion 2e straightens to the neutral position shown in FIG. 12.

The smooth, flexible outer skin 18a of the sixth embodiment covers the radial expansion restraint 14. The surface of the entire bendable portion 2e is therefore smooth. Thus, the endoscope can be smoothly inserted, and neither the surgical subject nor the endoscope are easily damaged. Further, tissue or bodily fluids are not caught in the radial expansion restraint 14, such that it is easy to clean the bendable portion 2e, keeping it clean and sterile.

Figure 14:
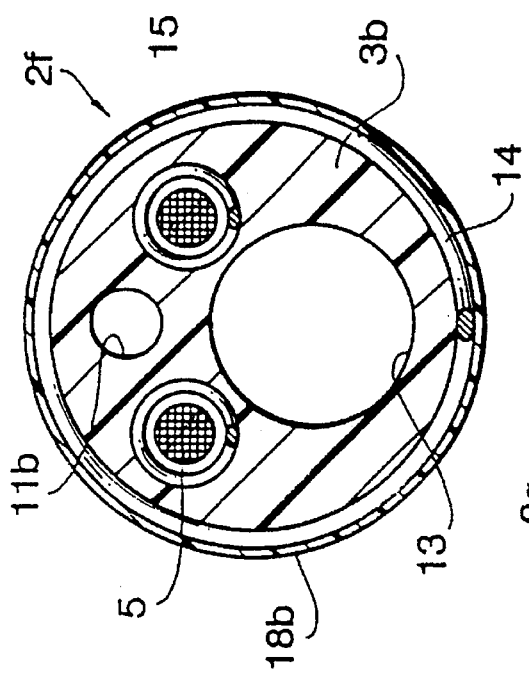
FIG. 14 is a cross-sectional front view of a bendable endoscope portion according to a seventh embodiment of the present invention.
Figure 15:
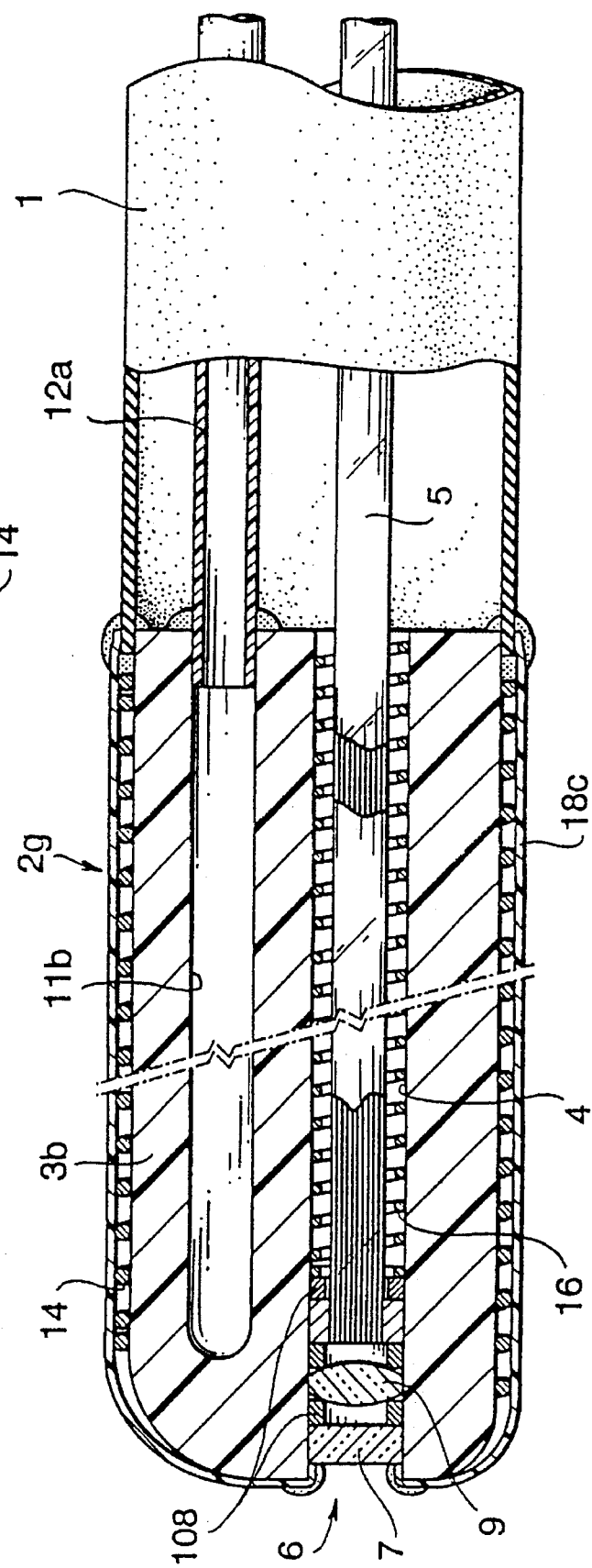
FIG. 15 is a cross-sectional side view of a bendable endoscope portion according to an eighth embodiment of the present invention.

FIGS. 14 and 15 show bendable portions of an endoscope according to a seventh and an eight embodiment of the present invention. FIG. 14 shows a distal end 2f of an endoscope of the seventh embodiment, generally similar to the second embodiment shown in FIG. 5. As shown in FIG. 14, the bendable portion 2f of the endoscope, and the encircling radial expansion restraint 14, are covered by a flexible outer skin 18b. FIG. 14 shows a distal end 2g of an endoscope of the eight embodiment, generally similar to the third described embodiment, in which the bendable portion 2g is covered by a flexible outer skin 18c. In the eight embodiment shown in FIG. 15, the flexible outer skin 18c is formed as a tube before it is attached to the bendable portion 2g. In both the seventh and eighth embodiments of a bendable portion 2f and 2g of an endoscope according to the present invention, a smooth bendable portion 2f or 2g may be easily assembled by sequentially attaching the radial expansion restraint 16 and the smooth and protective flexible outer skin 18b or 18c.

FIG. 16 shows a bendable portion 2h of an endoscope according to a ninth embodiment of the present invention. An endoscope of the ninth embodiment is generally similar to the sixth embodiment shown in FIG. 12. The ninth embodiment is different in that the fluid applying tube 12b is a metal tube, for example, a stainless steel tube, allowing high fluid pressures. It is preferable that the metal fluid applying tube 12b is flexible and is able to resist fluid pressures of more than 10 atm. A silicon adhesive 100 is preferably used to join the metal fluid applying tube and the elastic body 3b, but the adhesiveness of the silicon adhesive 100 to a metal tube is unsatisfactory. Therefore, the outer diameter of the fluid applying metal tube 12b, at the connection to the elastic body 3b, is covered by a glass coating 121, as shown in FIG. 17. The glass coating 121, bonded to the fluid applying metal tube 12b, is fastened to the elastic body 3b using a silicon adhesive 100. The glass coating 121 has good adhesiveness to the silicon adhesive 10, so that the fluid applying tube 12b is therefore strongly connected to the elastic body 3b. The glass coating 121 is formed by applying a glass paste to the fluid applying metal tube 12b, and sintering the paste at a temperature between 600 and 800 degrees Celsius.

Figure 18:
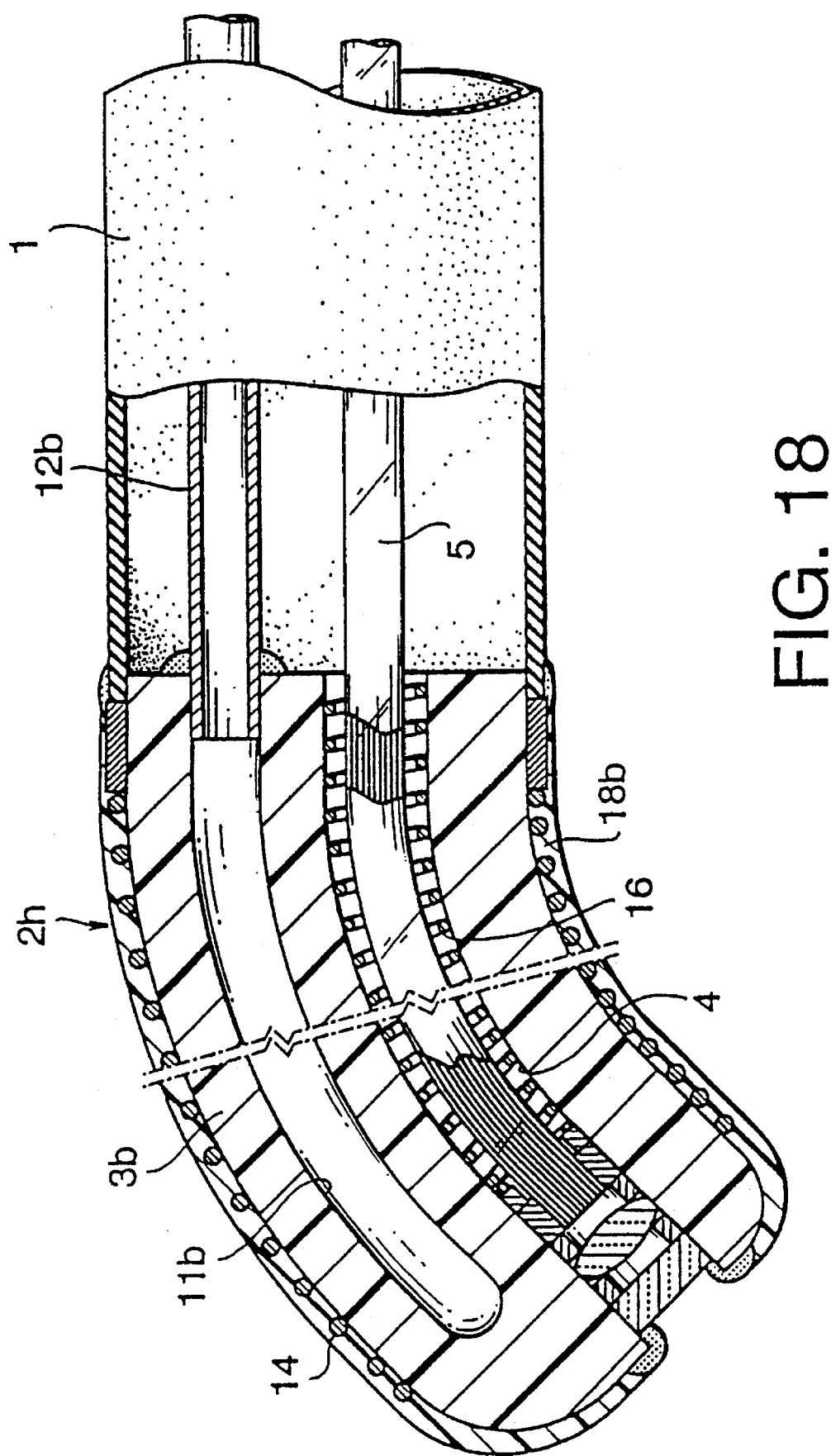
FIG. 18 is a cross-sectional side view of the ninth embodiment during bending.

As shown in FIG. 16, a metal ring 19 encircles the attachment end of the elastic body 3b to protect the connection between the fluid applying tube 12b and the elastic body 3b. The bending of the ninth embodiment is shown in FIG. 18. When the fluid in the pressure chamber 11b is pressurized, the bendable portion 2h bends as shown in FIG. 18. The attached end of the elastic body 3b, held at the metal ring 19, does not bend, such that bending stress is not transmitted to the connection between the fluid applying tube 12b and the elastic body 3b. The metal ring 19 prevents the rear end portion of the elastic body 3b from bending, even when the elastic body 3b is repeated bent. The connection at the silicon adhesive 100 is protected from detaching from the elastic body 3b. Preferably, the length of the metal ring 19 in its axial direction is 5 mm, sufficient to protect the adhesive 100 connection. The ninth embodiment of the bendable portion 2h of an endoscope according to the present invention therefore allows high pressures for bending the bendable portion 2h, by virtue of the securely attached metal fluid applying tube 12b and metal ring 19.

Figure 19:
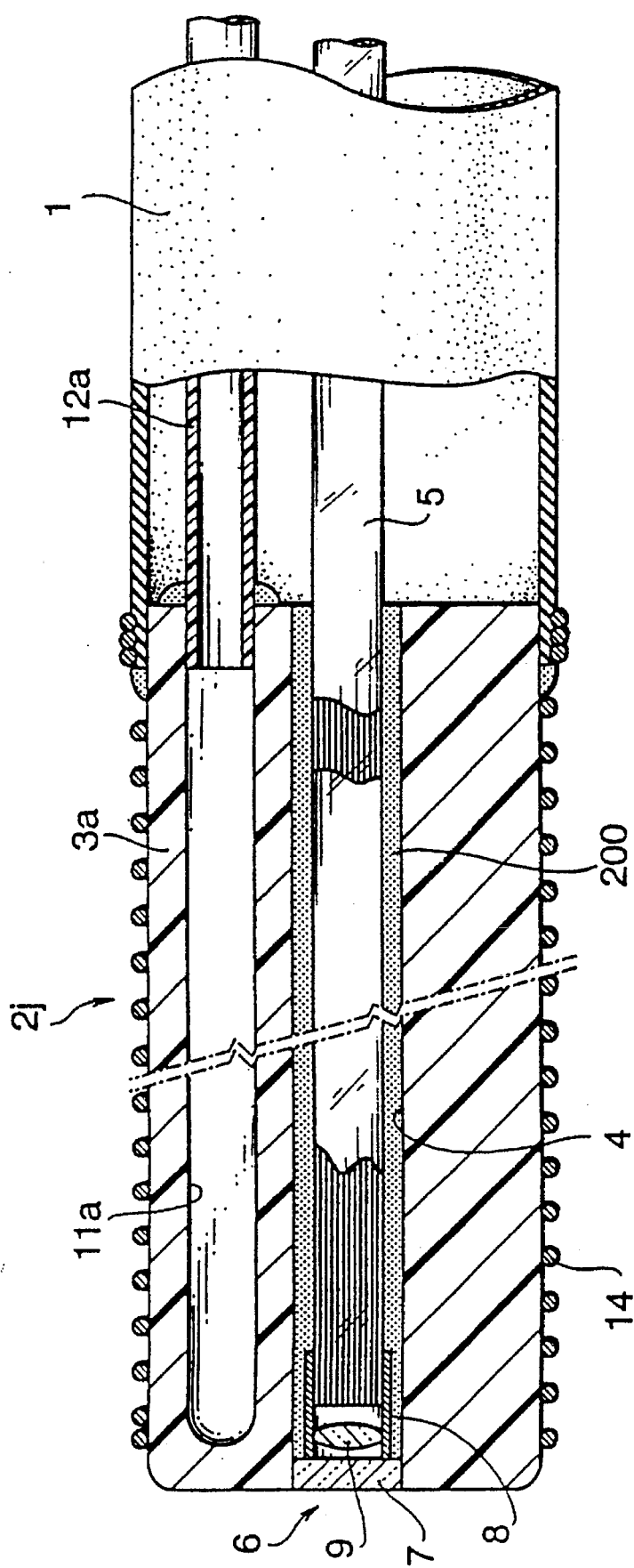
FIG. 19 is a cross-sectional side view of a bendable endoscope portion according to a tenth embodiment of the present invention.
Figure 20:
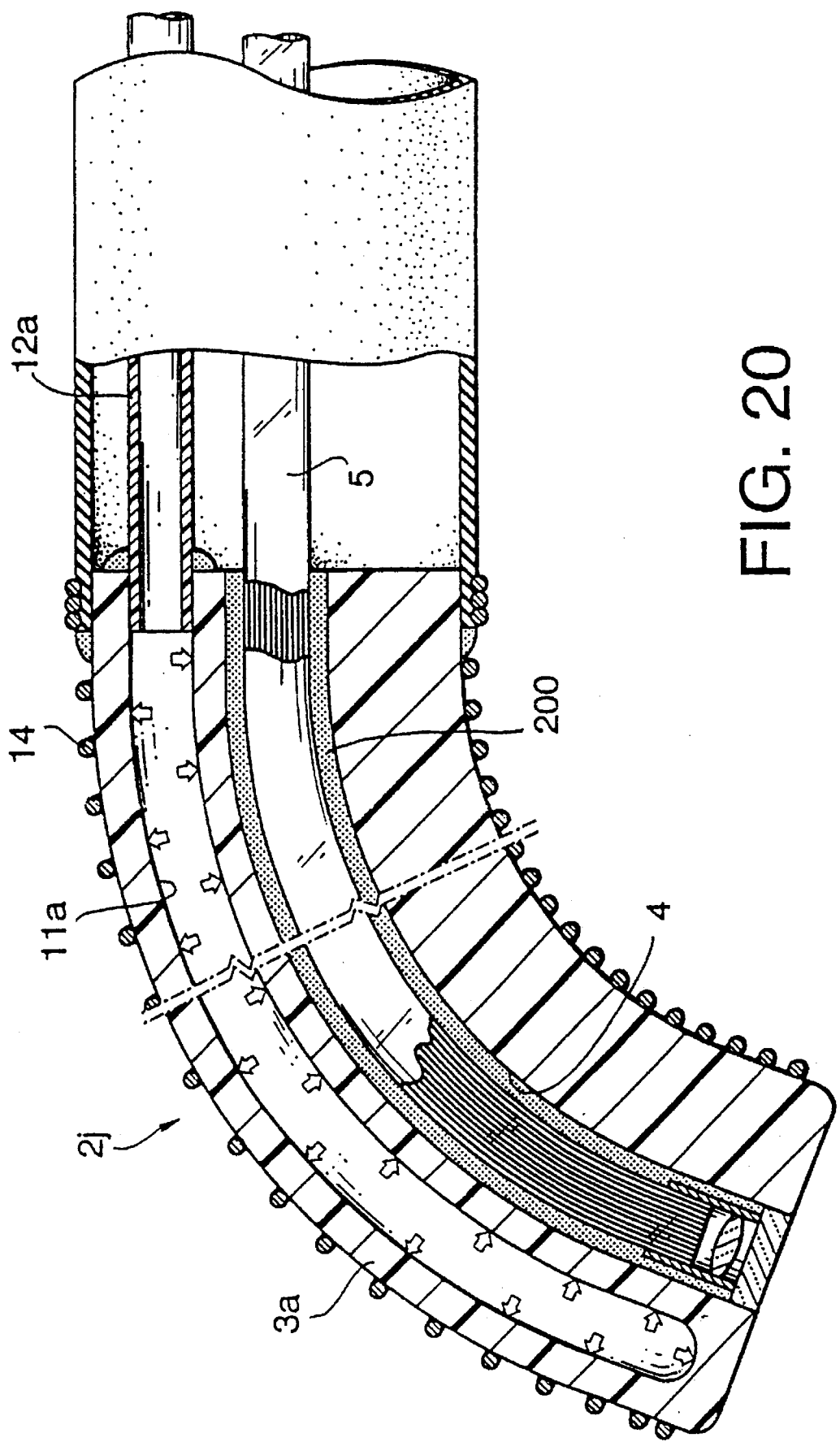
FIG. 20 is a cross-sectional side view of the tenth embodiment during bending.

FIG. 19 shows a bendable portion 2j of an endoscope according to a tenth embodiment of the present invention. An endoscope of this embodiment is generally the same as the first embodiment shown in FIG. 1. The tenth embodiment is different in that a lubricant 200 is applied to the inner surface of the through channel 4, and to the outer surface of the image guide fiber bundle 5. The lubricant 200 is preferably formed of alumina particles of 2 to 6 μm diameter. When the fluid in the pressure chamber 11a is pressurized, the bendable portion 2j of the tenth embodiment bends as shown in FIG. 20. The lubricant 200 can be alternatively, molybdenum disulfide, magnesium oxide or ethylene tetrafluoride, using particles from 0.1 μm to 20 μm in diameter. According to the tenth embodiment of a bendable portion 2j of an endoscope, the lubricant 200 reduces friction between the image guide fiber bundle 5 and the through channel 4. The image guide fiber bundle 5 is therefore protected from frictional damage from the through channel 4. Moreover, the lubricant can be applied to other elements of the bendable portion 2j, such as a light guide fiber bundle, for example.

Figure 21:
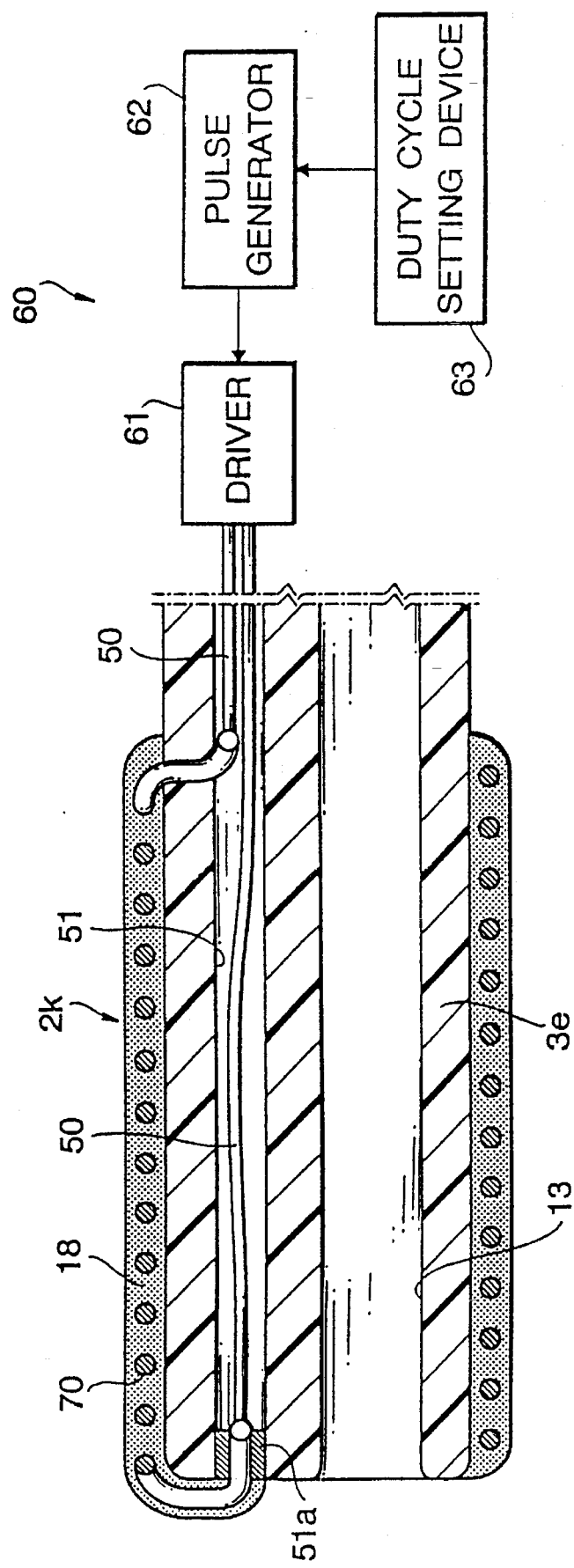
FIG. 21 is a cross-sectional side view of a bendable endoscope portion according to an eleventh embodiment of the present invention.

FIG. 21 shows a bendable portion 2k of an endoscope according to an eleventh embodiment of the present invention. The bendable portion 2k of an endoscope of the eleventh embodiment is different in that the bending mechanism uses a shape memory alloy, instead of the pressure chamber as in the above mentioned embodiments.

A bending mechanism using a shape memory alloy is known from the prior art. For example, Japanese Patent laid-open publication Nos. Hei 1-304416 and Hei 1-315675 disclose a bending actuator having a plurality of shape memory alloy springs. When an electric current is applied to the springs, the springs are resistively heated (Joule heating) and expand linearly, increasing their coiled length, by virtue of the properties of the shape memory alloy, bending the actuator. However, the bending mechanism disclosed in the above-mentioned publications needs a large space to arrange the shape memory alloy springs. It is therefore difficult to make a slender endoscope with this technique.

Japanese Patent laid open publication No. Hei 3-173371 discloses a bending actuator having a thin plate formed from a shape memory alloy. The construction disclosed in this publication may be effective for the purpose of building a slender endoscope. However, the state of the art in forming a shape memory alloy does not allow forming a thin plate easily. The solution disclosed in Japanese Patent laid-open publication No. Hei 3-173371 is therefore difficult to implement. The object of the eleventh embodiment is to allow the construction of a thin diameter endoscope with a bending mechanism using a shape memory alloy.

As shown in FIG. 21, the endoscope of the eleventh embodiment comprises a bendable portion 2k and a control circuit 60. FIG. 22 shows a front cross-sectional view of the bendable portion 2k according to the eleventh embodiment.

The bendable portion 2k comprises an elastic body 3e through which a forceps channel 13, an electric channel 51, an image guide fiber channel 52 and an illumination fiber channel 53 are formed. Preferably, the diameter of the forceps channel 13 is 1.2 mm, and the diameter of each of the remaining channels 51, 52, and 53 is preferably 0.35 mm. The channels are shown in detail in FIG. 22. Electric lines 50 are arranged in the electric channel 51, and an image guide fiber bundle 5 and a light guide fiber bundle 15 are arranged in the image guide fiber channel 52 and the light guide fiber channel 53, respectively. The bendable portion 2k is preferably equal to or less than 2 mm in diameter and is preferably 30 mm in length.

The bendable portion 2k is encircled by a bending coil 70. The bending coil 70 is formed of a shape memory alloy, preferably a wire of 0.1 mm or smaller. The bending coil 70 is shaped to fit the bendable portion; that is, the bending coil is the same inner diameter as the outer diameter of the bendable portion and of the same coiled length as the length of the bendable portion 2k. Preferably, the winding pitch of the coil 70 in the axial direction is 0.3 mm. The bending coil 70 is completely embedded in a flexible outer skin 18. Therefore the bendable portion 2k is covered except for the above-mentioned channels. The flexible outer skin 18 is both electrically and thermally insulating. The thickness of the flexible outer skin is preferably 0.1 to 0.2 mm.

Both ends (terminals) of the bending coil 70 are drawn into the electric channel 51, and are connected to the electric lines 50. The electric channel 51 opening is sealed by an adhesive sealing material 51a. The electric lines 50 are connected to a drive 61 of the control circuit 60. The driver 61 is used to apply an electric current to the electric lines 50, for example, 1.5 amperes. The driver 61 is controlled by a pulse generator 62 so that the output waveform of the driver 61 is the same waveform as the applied pulses from the pulse generator 62. A duty cycle setting device 63 sets the on/off duty cycle of the pulse generator 62. Thus, the duty cycle setting device 63 controls the duty cycle of the pulsed-waveform electric current applied from the driver 61 to the electric lines 50.

A predetermined bent shape is retained ("memorized") by heat treating the shape memory alloy of the bending coil 70. The coil is formed in the predetermined bent shape such that the coil axis of the bending coil is bent to a predetermined curved shape, corresponding to a predetermined bent shape of the elastic body 3e. The shape memory alloy of the bending coil 70 returns to the predetermined bent shape when its temperature reaches or exceeds certain values. Therefore, when a pulsed-waveform electric current is applied to the bending coil 70 from the driver 61 through the electric lines 50, the bending coil 70 is resistively heated (Joule heating) and bends the bendable portion 2k. The bending angle of the bendable portion 2k can be changed by controlling the duty cycle of the applied pulsed-waveform electric current.

Preferably, the bendable portion 2k, bent by the shape memory alloy bending coil 70, bends to a radius of a curvature of 25 mm, as shown in FIG. 23, when the temperature of the bending coil 70 is from 40 to 50 degrees Celsius. When the temperature of the bending coil 70 lowers, the bending coil 70 and the bendable portion 2k straightens to the shape shown in FIG. 21. The shape memory alloy is selected from a Ti—Ni system or a Cu system. By virtue of the shape memory alloy bending coil 70 of the eleventh embodiment, surrounding the elastic body 3e, the bendable portion 2k may be made thin.

As described, each of the embodiments of the present invention allow the construction of a very slender endoscope. Furthermore, even though the bendable portion may be made very slender, the bending mechanisms described allow a large bending amount relative to the length of the bendable portion.

The present disclosure relates to subject matter contained in Japanese patent application Nos. Hei 5-249131 (filed on Oct. 5, 1993), Hei 5-286348 (filed on Nov. 16, 1993), Hei 5-296529 (filed on Nov. 26, 1993), Hei 5-299497 (filed on Nov. 30, 1993), Hei 6-161941 (filed on Jul. 14, 1994), Hei 6-199197 (filed on Aug. 24, 1994) which are expressly incorporated herein by reference in their entireties.

What is claimed is:

1. A bendable portion of an endoscope, said bendable portion attached to an insertion tube of an endoscope, said bendable portion comprising:

an elastic body, connected to an insertion tube and formed substantially as an elongated cylinder, said elastic body being elongated in an axial direction;

a channel for inserting an internal member therethrough, said channel being formed through said elastic body along said axial direction of said elastic body;

a pressure chamber formed in a peripheral portion of said elastic body, displaced from a central axis of said elastic body and parallel to said central axis;

a fluid applying tube connected to said pressure chamber for pressurizing and depressurizing said pressure chamber with a fluid so that said pressure chamber expands and contracts and said elastic body bends; and an expansion restraining member encircling said elastic body, said expansion restraining member preventing expansion of said elastic body in a radial direction and allowing expansion and contraction only along said axial direction when said pressure chamber is pressurized and depressurized.

2. The bendable portion of an endoscope according to claim 1, wherein a plurality of said pressure chambers are arranged around said central axis.

3. The bendable portion of an endoscope according to claim 2, wherein said expansion restraining member comprises a coil spring.

4. The bendable portion of an endoscope according to claim 3, wherein said coil spring is formed of metal wire.

5. The bendable portion of an endoscope according to claim 1, wherein said expansion restraining member comprises a coil spring.

6. The bendable portion of an endoscope according to claim 5, wherein said coil spring is formed of metal wire.

7. The bendable portion of an endoscope according to claim 1, wherein said expansion restraining member is embedded in said elastic body.

8. The bendable portion of an endoscope according to claim 7, wherein said expansion restraining member comprises a coil spring.

9. The bendable portion of an endoscope according to claim 8, wherein said coil spring is formed of metal wire.

10. The bendable portion of an endoscope according to claim 1, further comprising a flexible outer skin, said flexible outer skin covering said expansion restraining member.

11. The bendable portion of an endoscope according to claim 1, further comprising said internal member being inserted in said channel, and a crush-resistant member arranged around said internal member to protect said internal member when said elastic body bends.

12. The bendable portion of an endoscope according to claim 11, wherein said crush-resistant member comprises a coil spring formed of metal wire.

13. The bendable portion of an endoscope according to claim 11, wherein said crush-resistant member is arranged in said channel.

14. The bendable portion of an endoscope according to claim 11, wherein said crush-resistant member is embedded in said elastic body and is arranged surrounding said channel.

15. The bendable portion of an endoscope according to claim 1, wherein a fluid applied by said fluid applying tube is gaseous.

16. The bendable portion of an endoscope according to claim 1, wherein said pressure chamber and said fluid applying tube are filled by a transparent liquid to transmit an illuminating light beam therethrough, and a window for transmitting said illuminating light beam is formed at an end of said pressure chamber.

17. The bendable portion of an endoscope according to claim 16, further comprising an illumination lens arranged in said window of said pressure chamber.

18. The bendable portion of an endoscope according to claim 17, further comprising a seal plate arranged in said window of said pressure chamber behind said illuminating lens, to form an air gap between said illuminating lens and said seal plate.

19. The bendable portion of an endoscope according to claim 1, wherein said fluid applying tube comprises a metal tube.

20. The bendable portion of an endoscope according to claim 19, wherein an end portion of said fluid applying tube, connected to said elastic body at said pressure chamber, is coated by a glass coating, and an adhesive is applied between said glass coating and said elastic body at said connection.

21. The bendable portion of an endoscope according to claim 1, further comprising a ring encircling an attachment end potion of said elastic body adjacent to an attachment to said insertion tube.

22. The bendable portion of an endoscope according to claim 1, wherein said internal member is inserted in said channel, and an inner surface of said through channel and an outer surface of said internal member are coated by a lubricant.

23. The bendable portion of an endoscope according to claim 22, wherein said internal member is an optical fiber bundle.

24. The bendable portion of an endoscope according to claim 22, wherein said lubricant is formed of particles.

25. The bendable portion of an endoscope according to claim 24, wherein said particles are alumina.

26. The bendable portion of an endoscope according to claim 25, wherein said particles have a diameter of 2 to 6 µm.

27. The bendable portion of an endoscope according to claim 24, wherein said particles are selected from the group consisting of molybdenum disulfide, magnesium oxide, and ethylene tetrafluoride.

28. The bendable portion of an endoscope according to claim 27, wherein said particles have a diameter of 0.1 to 20 µm.

29. The bendable portion of an endoscope according to claim 1, wherein said fluid is a liquid.

30. A bendable portion of an endoscope, said bendable portion connected to an insertion tube of an endoscope, said bendable portion comprising:

an elastic body, connected to an insertion tube and formed substantially as an elongated cylinder, said elastic body being elongated in an axial direction;

a channel having an internal member inserted therethrough, said channel being formed through said elastic body along axial direction of said elastic body;

a pressure chamber formed in a peripheral portion of said elastic body, displaced from a central axis of said elastic body and parallel to said central axis;

a fluid applying tube connected to said pressure chamber for pressurizing and depressurizing said pressure chamber so that said pressure chamber expands and contracts and said elastic body bends;

an expansion restraining member encircling said elastic body, wherein said expansion restraining member prevents expansion of said elastic body in a radial direction and allows expansion and contraction only along said axial direction when said pressure chamber is pressurized and depressurized; and a crush-resistant member arranged around said internal member to protect said internal member when said elastic body bends.

31. The bendable portion of an endoscope according to claim 30, wherein said crush-resistant member comprises a coil spring formed of metal wire.

32. A bendable portion of an endoscope, said bendable portion connected to an insertion tube of an endoscope, said bendable portion comprising:

an elastic body, connected to an insertion tube and formed substantially as an elongated cylinder;

a channel for inserting an internal member therethrough, said channel being formed through said elastic body along an axial direction of said elastic body;

a pressure chamber formed in a peripheral portion of said elastic body, displaced from a central axis of said elastic body and parallel to said central axis, said pressure chamber formed as a through channel completely blocked by a transparent member at a remote end of said bendable portion;

a fluid applying tube connected to said pressure chamber for pressurizing and depressurizing said pressure chamber so that said pressure chamber expands and contracts and said elastic body bends; and wherein said pressure chamber and said fluid applying tube are filled with a transparent liquid to transmit an illuminating light beam therethrough, and a window for transmitting said illuminating light beam is formed at an end of said pressure chamber.

33. The bendable portion of an endoscope according to claim 32, further comprising an illumination lens arranged in said window of said pressure chamber.

34. The bendable portion of an endoscope according to claim 33, wherein said transparent member comprises a seal plate, said seal plate being arranged in said pressure chamber behind said illuminating lens to form an air gap between said illuminating lens and said seal plate.

35. A bendable portion of an endoscope, said bendable portion connected to an insertion tube of said endoscope, an bendable portion comprising:

an elastic body, connected to an insertion tube and formed substantially as an elongated cylinder;

a channel for inserting an internal member therethrough, said channel being formed through said elastic body along an axial direction of said elastic body;

a pressure chamber formed in a peripheral portion of said elastic body, displaced from a central axis of said elastic body and parallel to said central axis, said pressure chamber formed as a through channel completely blocked by a transparent member at a remote end of said bendable portion;

a fluid applying tube connected to said pressure chamber for pressurizing and depressurizing said pressure chamber so that said pressure chamber expands and contracts and said elastic body bends;

an illumination lens arranged in said pressure chamber, said transparent member including a seal plate, said seal plate being arranged in said pressure chamber behind said illuminating lens to form an air gap between said illuminating lens and said seal plate;

wherein said pressure chamber sand said fluid applying tube are filled with a transparent liquid to transmit an illuminating light beam therethrough.

\* \* \* \* \*

UNITED STATES PATENT AND TRADEMARK OFFICE
CERTIFICATE OF CORRECTION

PATENT NO.   : 5,577,992
DATED        : November 26, 1996
INVENTOR(S)  : T. CHIBA et al.

It is certified that error appears in the above-indentified patent and that said Letters Patent is hereby corrected as shown below:

At column 13, line 1 (claim 21, line 3), change "potion" to ---portion---.

At column 14, line 33 (claim 35, line 2), change "said endoscope" to ---an endoscope---.

At column 14, lines 33-34 (claim 35, lines 2-3), change "an bendable" to ---said bendable---.

At column 14, line 56 (claim 35, line 24), change "sand" to ---and---.

Signed and Sealed this

First Day of April, 1997

Attest:

BRUCE LEHMAN

Attesting Officer

Commissioner of Patents and Trademarks